(12) United States Patent
Genco

(10) Patent No.: US 10,485,576 B2
(45) Date of Patent: Nov. 26, 2019

(54) CIRCUMCISION SET AND METHOD FOR EXECUTING A CIRCUMCISION ON A MAN'S PENIS

(71) Applicant: Genco Research & Development B.V., Amsterdam (NL)

(72) Inventor: Sükrü Genco, Amsterdam (NL)

(73) Assignee: Genco Research & Development B.V., Amsterdam (NL)

( * ) Notice: Subject to any disclaimer, the term of this patent is extended or adjusted under 35 U.S.C. 154(b) by 228 days.

(21) Appl. No.: 15/550,793

(22) PCT Filed: Feb. 11, 2016

(86) PCT No.: PCT/NL2016/050099
§ 371 (c)(1),
(2) Date: Aug. 14, 2017

(87) PCT Pub. No.: WO2016/130007
PCT Pub. Date: Aug. 18, 2016

(65) Prior Publication Data
US 2018/0036027 A1 Feb. 8, 2018

(30) Foreign Application Priority Data
Feb. 12, 2015 (NL) ...................................... 2014281

(51) Int. Cl.
*A61B 17/326* (2006.01)
(52) U.S. Cl.
CPC ................................. *A61B 17/326* (2013.01)
(58) Field of Classification Search
CPC ..... A61B 17/326; Y10T 24/26; Y10T 24/262; Y10T 24/264; Y10T 24/266; Y10T 24/268; Y10T 24/149
See application file for complete search history.

(56) References Cited

U.S. PATENT DOCUMENTS 2,544,037 A 3/1951 Moseley
4,183,120 A * 1/1980 Thorne ................. B25B 25/005
24/16 R (Continued)

FOREIGN PATENT DOCUMENTS

CN 201160878 12/2008
CN 202859243 4/2013

(Continued)

OTHER PUBLICATIONS

International Search Report and the Written Opinion dated Jun. 2, 2016 From the International Searching Authority Re. Application No. PCTNL2016/050099. (12 Pages).

*Primary Examiner* — Tuan V Nguyen

(57) ABSTRACT

Circumcision set used in a method for executing a circumcision on a man's penis, employing a male member and a female member that are releasably connectable to each other, and including the steps of:
providing that the male member and the female member are connected;
receiving in the female number a forward end of a human's penis;
positioning the penis' foreskin over said female member's outer circumference;
providing a closure device circumferentially around the foreskin's outer side opposite to the female member so as to entrap and clamp the foreskin between the closure device and the female member to prevent blood flowing to the foreskin;
removing the foreskin;
releasing the closure device; and
removing the female member;
thus providing a circumcised penis.

10 Claims, 2 Drawing Sheets

(56) References Cited

Figures 5, 6, 7:
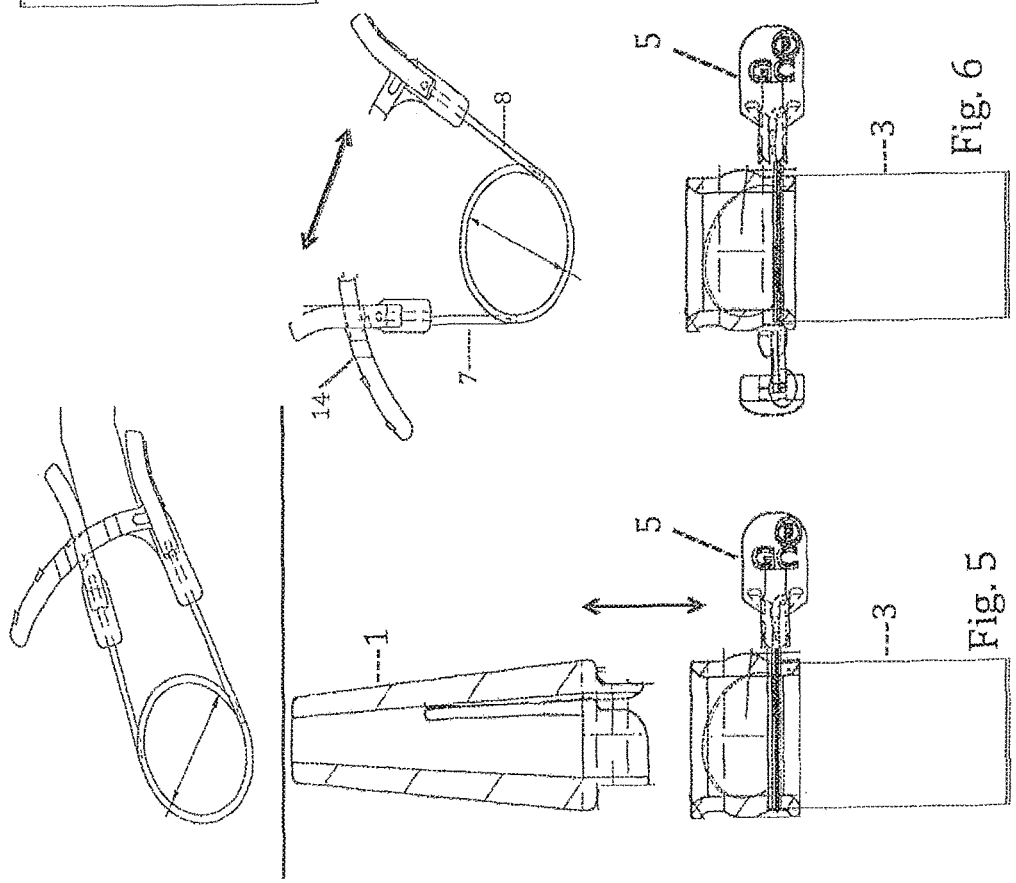

U.S. PATENT DOCUMENTS 4,491,136 A 1/1985 LeVeen
2012/0203242 A1 8/2012 Fuerst et al.

FOREIGN PATENT DOCUMENTS

WO WO 2007/028378 3/2007
WO WO 2013/079077 6/2013

* cited by examiner

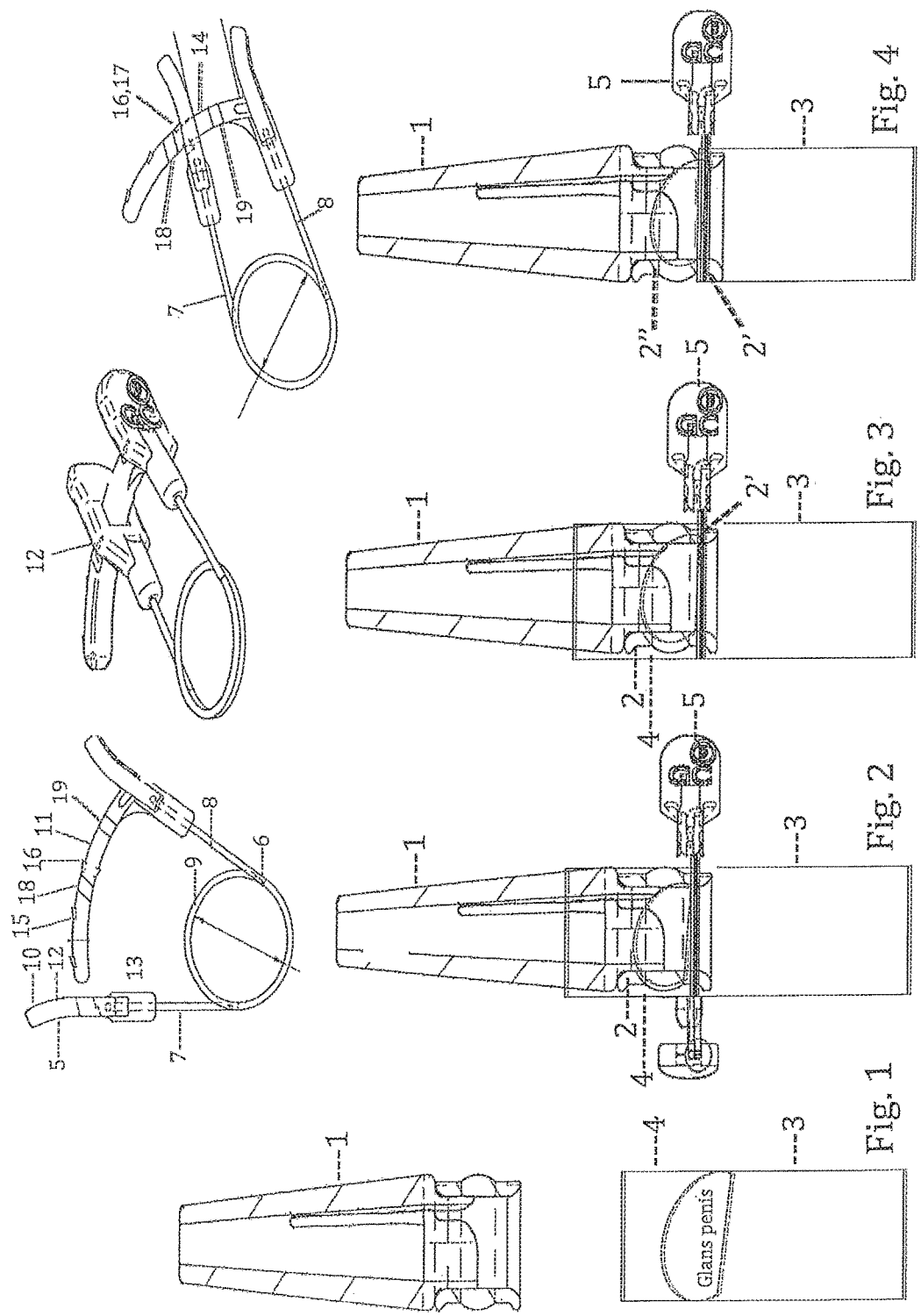

CIRCUMCISION SET AND METHOD FOR EXECUTING A CIRCUMCISION ON A MAN'S PENIS

RELATED APPLICATIONS

This application is a National Phase of PCT Patent Application No. PCT/NL2016/050099 having International filing date of Feb. 11, 2016, which claims the benefit of priority of Netherlands Patent Application No. 2014281 filed on Feb. 12, 2015. The contents of the above applications are all incorporated by reference as if fully set forth herein in their entirety.

FIELD AND BACKGROUND OF THE INVENTION

The invention relates to a circumcision set comprising a male member and a female member that are releasably connectable to each other and that define a released position and a connected position with respect to each other.

U.S. Pat. No. 4,491,136 discloses a circumcision set comprising a male member comprising a ring with an annular groove, and a female member embodied as a plastic ring, wherein the male member is inserted and fits under the foreskin and the female member over the foreskin so that the plastic ring of the female member can be moved up to a position in register with the ring of the male member, which superimposes it over the ring on the male member underneath the foreskin with the foreskin caught in between the two. Executing the circumcision with this prior art circumcision set requires the use of a separate clamp instrument which makes the set relatively hard to handle and less suitable for mass circumcisions.

US2012/0203242 teaches a circumcision set comprising a male member and a female member that are releasably connectable to each other and that define a released position and a connected position with respect to each other, wherein in the connected position the male member and the female member define a longitudinal tube for receiving therein a forward end of a human's penis, wherein the female member is construed to arrange that the penis' foreskin is positionable over said female member's outer circumference, and wherein the set further comprises a closure device embodied as a ring-shaped spring with at least one turn or turns comprising two legs at opposite sides of the spring's turn or turns for placement circumferentially around the foreskin's outer side opposite to the female member so as to entrap the foreskin between the closure ring and the female member to prevent blood flowing to the foreskin, wherein during use each turn fully envelopes the foreskin. Placement of the ring of this known circumcision set appears to be rather complicated.

SUMMARY OF THE INVENTION

It is an object of the invention to improve or at least alleviate some or all of the drawbacks of the prior art circumcision set.

It is a further object of the invention to provide a circumcision set that is foolproof and only requires immediately obvious and simple handling, without need to resort to any instruction manual.

According to the invention a circumcision set and a method to execute such a circumcision are proposed in accordance with the features of one or more of the appended claims.

The circumcision set of the invention has the feature that the legs of the closure device are connectable to each other wherein a first leg of the legs of the closure device supports a head provided with an opening for receiving a strap, and the second leg of said legs supports the strap, which is equipped with at least one protrusion which is arranged to hook behind an edge of said opening through which the strap is insertable, and that the strap is provided with first and second protrusions respectively defining temporary and final closing positions. Practice has proven that this arrangement is beneficial for the ease of handling and placement of the closure device. Using the first protrusion that constitutes a temporary position enables an easy initial placement of the circumcision set. In the temporary position the circumcision set can be easily checked for its proper placement on the human's penis. After that and following the initial placement, the closure device of the circumcision set can be moved to its final closing position.

Preferably further the strap is provided with a predefined weaker portion or portions to define preferred cutting positions. These preferred cutting positions are employed to cut loose ends and for easy removing the closure device after it has been in place on the penis for some time (mostly five days or more).

The circumcision set of the invention thus enables easy handling during its placement, and provides that a method can be employed in which subsequently and easily the following steps are executed:
providing that the male member and the female member are connected;
receiving in the female number a forward end of a human's penis;
positioning the penis' foreskin over said female member's outer circumference;
providing a closure device circumferentially around the foreskin's outer side opposite to the female member so as to entrap and clamp the foreskin between the closure device and the female member to prevent blood flowing to the foreskin;
removing the foreskin;
releasing the closure device; and
removing the closure device and the female member.

Preferably in this method removing the foreskin is executed substantially immediately after entrapping and clamping the foreskin between the closure device and the female member.

Further preferably releasing the closure device and removing the closure device and female member is executed at least five days after placement.

To assist in the ease of handling of the circumcision set of the invention it is preferred that the female member is equipped with a circumferential first recess on the far end distant from the male member and designed for receiving therein the foreskin's part that is entrapped between the female member and the closure device.

The ease of use of the circumcision set of the invention is further promoted by the feature that the female member is equipped with a circumferential second recess on the near end close to the male member to provide a preferential position at which foreskin is removed from the penis' remainder.

In a preferred embodiment of the invention the legs of the closure device are at their free extremities provided with cooperating parts embodied as a tiewrap connector. This makes handling of the closure device and completing the entrapment and clamping of the foreskin very easy.

The invention will hereinafter be further elucidated with reference to the drawing of an exemplary embodiment of a circumcision set and a method of executing a circumcision according to the invention that is not limiting as to the appended claims.

BRIEF DESCRIPTION OF THE SEVERAL VIEWS OF THE DRAWING(S)

In the drawing:

FIGS. 1, 2, 3, 4, 5, 6 and 7, each of the figures comprising a top part and a lower part, show schematically the sequential execution of a circumcision utilizing a circumcision set according to the invention.

Whenever in the figures the same reference numerals are applied, these numerals refer to the same parts.

DESCRIPTION OF SPECIFIC EMBODIMENTS OF THE INVENTION

Making first reference to the top part of FIG. 1 a male member 1 and a female member 2 that are releasably connectable to each other are shown in their connected position with respect to each other. They are however releasable from each other as will become clear from the following disclosure.

In the connected position of the male member 1 and the female member 2 shown in the top part of FIG. 1, said members define a longitudinal tube for receiving in said female member 2 a forward end of a human's penis 3, which is independently shown in the lower part of FIG. 1. In the lower part of FIG. 2 the forward end of the penis 3 is received in the female member 2.

The lower part of FIG. 2 further shows that the female member 2 is construed to arrange that the penis' foreskin 4 is positionable over the outer circumference of the female member 2. Further both the top part and the lower part of FIG. 2 show that the circumcision set of the invention also comprises a closure device 5. The lower part of FIG. 2 shows that the closure device 5 is placed circumferentially around the foreskin 4 opposite to the female member 2.

In the top part of FIG. 2 the closure device 5 is shown separately in a side view, from which it is clear that the closure device 5 is embodied as a spring 6 comprising two legs 7, 8 at opposite sides of the spring's turn or turns 9, so that during use each turn 9 will fully envelope the foreskin 4, and wherein said legs are connectable to each other. In the lower part of FIG. 2 said closure device 5 is positioned at its eventual intended location over the outer circumference of the female member 2, while it is still in its released position as shown in the top part of FIG. 2, that means without yet being in the clamped position wherein the foreskin 4 is trapped and clamped between the closure device 5 and the female member 2.

Turning now to FIG. 3, it is shown that the closure device 5 is closed so as to fully envelop and clamp the foreskin 4 between the closure device 5 and the female member 2 and to entrap in this way the foreskin 4 between the closure device 5 and the female member 2 to prevent blood flowing to the foreskin 4. To support easy placement of the closure device 5, the female member 2 is equipped with a circumferential first recess 2' on the far end distant from the male member 1, which is designed for receiving therein the part of the foreskin 4 that is entrapped between the female member 2 and the closure device 5.

FIG. 4 depicts that after placement and clamping of the closure device 5, the foreskin 4 is cut away and removed, for which purpose preferably the female member 2 is equipped with a circumferential second recess 2" on the near end close to the male member 1 to provide a preferential position at which foreskin 4 is removed from the penis' remainder. Next the male member 1 can be released from the female member 2 so as to leave the female member 2 and the closing device 5 clamped thereon behind on the penis 3. This is depicted in FIG. 5.

After a prescribed amount of time, for instance five days, the closure device 5 and the female member 2 can be removed from their position on the penis 3 as shown in FIG. 6. The top part of FIG. 6 shows the release of the closure device 5, after which this closure device 5 and the female member 2 can be removed from the penis 3. The result being the circumcised penis 3 is finally shown in FIG. 7.

Beneficial features of the closure device 5 are further elucidated in the following with reference to some of the above-mentioned figures.

The top part of FIG. 2 shows that the legs 7, 8 of the closure device 5 are at their free extremities provided with cooperating parts 10, 11 embodied as a tiewrap connector (see also the top part of FIG. 3). The top part of FIG. 2 shows that a first leg 7 of the legs of the closure device 5 supports a head 12 provided with an opening 13 for receiving a strap 14, wherein the second leg 8 of said legs supports the strap 14.

The strap 14 is equipped with at least one protrusion 15, 16 which is arranged to hook behind an edge 17 of said opening 13 through which the strap 14 is insertable. First protrusions 15 of the strap 14 define a temporary locked position of the strap 14 after its insertion through the opening 13, and second protrusions 16 define a final locking position when the strap 14 is inserted to the extent that it fully envelopes and clamps around the female member 2 with the foreskin 4 in between. This is shown in FIG. 3.

Making reference again to the top part of FIG. 2 it is shown that the strap 14 is preferably also provided with a predefined weaker portion or portions 18, 19 to define preferred cutting positions. The first weaker portion 18 is intended to enable easy removal of the part of the strap 14 that extends beyond the opening 13 when the closure device is in the clamped position and the first protrusion 15 hooks behind the edge 17 of the opening 13 (this is not shown in the figures, but clear for the artisan). The second weaker portion 19 is intended to enable easy opening of the closure device 5 as shown in the top part of FIG. 6, when the closure device 5 and the female member 2 can be removed from the then circumcised penis 3.

Although the invention has been discussed in the foregoing with reference to an exemplary embodiment of the method and circumcision set of the invention, the invention is not restricted to this particular embodiment which can be varied in many ways without departing from the gist of the invention. The discussed exemplary embodiment shall therefore not be used to construe the appended claims strictly in accordance therewith. On the contrary the embodiment is merely intended to explain the wording of the appended claims without intent to limit the claims to this exemplary embodiment. The scope of protection of the invention shall therefore be construed in accordance with the appended claims only, wherein a possible ambiguity in the wording of the claims shall be resolved using this exemplary embodiment.

What is claimed is:

1. Circumcision set comprising a male member (1) and a female member (2) that are releasably connectable to each other and that define a released position and a connected position with respect to each other, wherein in the connected position the male member (1) and the female member (2) define a longitudinal tube for receiving therein a forward end of a human's penis (3), wherein the female member (2) is construed to arrange that the penis' foreskin (4) is positionable over said female member's outer circumference, and wherein the set further comprises a closure device (5) for placement circumferentially around the foreskin's outer side opposite to the female member (2) so as to entrap the foreskin (4) between the closure device (5) and the female member (2) to prevent blood flowing to the foreskin (4), wherein the closure device (5) is embodied as a spring (6) comprising two legs (7, 8) at opposite sides of the spring's turn or turns (9), wherein during use each turn (9) fully envelopes the foreskin (4), wherein said legs (7, 8) are connectable to each other wherein a first leg (7) of the legs of the closure device (5) supports a head (10) provided with an opening (13) for receiving a strap (14), and the second leg (8) of said legs supports the strap (14), which is equipped with at least one protrusion (15, 16) which is arranged to hook behind an edge (17) of said opening (13) through which the strap (14) is insertable, and that the strap (14) is provided with first and second protrusions (15, 16) respectively defining temporary and final closing positions, wherein the strap (14) is provided with a predefined weaker portion or portions (18, 19) to define preferred cutting positions.

2. Circumcision set according to claim 1, wherein the female member (2) is equipped with a circumferential first recess (2') on a far end distant from the male member (1) and designed for receiving therein the foreskin's part that is entrapped between the female member (2) and the closure device (5).

3. Circumcision set according to claim 2, wherein the female member (2) is equipped with a circumferential second recess (2") on a near end close to the male member (1) to provide a preferential position at which foreskin (4) is removed from the penis' remainder.

4. Circumcision set according to claim 2, wherein the legs (7, 8) of the closure device (5) are at their free extremities provided with cooperating parts (10, 11) embodied as a tiewrap connector (12).

5. Circumcision set according to claim 1, wherein the female member (2) is equipped with a circumferential second recess (2") on a near end close to the male member (1) to provide a preferential position at which foreskin (4) is removed from the penis' remainder.

6. Circumcision set according to claim 5, wherein the legs (7, 8) of the closure device (5) are at their free extremities provided with cooperating parts (10, 11) embodied as a tiewrap connector (12).

7. Circumcision set according to claim 1, wherein the legs (7, 8) of the closure device (5) are at their free extremities provided with cooperating parts (10, 11) embodied as a tiewrap connector (12).

8. Circumcision set according to claim 1, wherein the female member (2) is equipped with a circumferential first recess (2') on a far end distant from the male member (1) and designed for receiving therein the foreskin's part that is entrapped between the female member (2) and the closure device (5).

9. Circumcision set according to claim 1, wherein the female member (2) is equipped with a circumferential second recess (2") on a near end close to the male member (1) to provide a preferential position at which foreskin (4) is removed from the penis' remainder.

10. Circumcision set according to claim 1, wherein the legs (7, 8) of the closure device (5) are at their free extremities provided with cooperating parts (10, 11) embodied as a tiewrap connector (12).

* * * * *